US012612221B2

(12) United States Patent
Bohnenstengel et al.

(10) Patent No.: US 12,612,221 B2
(45) Date of Patent: Apr. 28, 2026

(54) CLOSURE MECHANISM WITH LOCKING DEVICE FOR STERILE CONTAINERS, AND STERILE CONTAINER COMPRISING SAME

(71) Applicant: Aesculap AG, Tuttlingen (DE)

(72) Inventors: Philipp Bohnenstengel, Steisslingen (DE); Stefan Thomas, Tuttlingen (DE); Andreas Elisch, Dunningen (DE); Matthias Henke, Villingen-Schwenningen (DE)

(73) Assignee: Aesculap AG, Tuttlingen (DE)

( * ) Notice: Subject to any disclaimer, the term of this patent is extended or adjusted under 35 U.S.C. 154(b) by 185 days.

(21) Appl. No.: 17/917,431

(22) PCT Filed: Apr. 7, 2021

(86) PCT No.: PCT/EP2021/059018

§ 371 (c)(1),
(2) Date: Oct. 6, 2022

(87) PCT Pub. No.: WO2021/204847

PCT Pub. Date: Oct. 14, 2021

(65) Prior Publication Data

US 2023/0159234 A1      May 25, 2023

(30) Foreign Application Priority Data

Apr. 8, 2020     (DE) ..................... 10 2020 109 765.4

(51) Int. Cl.
B65D 45/22          (2006.01)
A61B 50/00          (2016.01)
(Continued)

(52) U.S. Cl.
CPC .............. B65D 45/22 (2013.01); A61B 50/30 (2016.02); E05B 65/52 (2013.01); A61B 2050/007 (2016.02)

(58) Field of Classification Search
CPC .. E05B 65/0014; E05B 65/52; E05B 65/5207; E05B 65/5215; E05B 65/523;
(Continued)

(56) References Cited

U.S. PATENT DOCUMENTS 3,338,449 A       8/1967   Swanson
4,179,143 A  *  12/1979   Shy .......................... E05C 1/04
                                                                      292/179
(Continued)

FOREIGN PATENT DOCUMENTS

CA             2272481 A1 *  11/1999   ............. B65D 45/24
DE     202013002232 U1      4/2013
(Continued)

OTHER PUBLICATIONS

Search Report received in German Application No. 10 2020 109 765.4 dated Dec. 8, 2020, with translation, 14 pages.
(Continued)

*Primary Examiner* — Christine M Mills
*Assistant Examiner* — Peter H Watson
(74) *Attorney, Agent, or Firm* — Christopher A. Rothe; CM Law

(57) ABSTRACT

A sterile container and a closure mechanism for the sterile container. The sterile container includes a container pan and a container lid. The container lid is lockable to the container pan by the closure mechanism. The closure mechanism has a bar element for undercut engagement with an engagement element arranged on the container pan or on the container lid and which forms an undercut. The bar element is positionable in a closed position, in which the bar element is operatively engaged with the engagement element via the undercut, and in a release position, in which the bar element and the engagement element are disengaged. The closure mechanism includes a locking element that is operatively
(Continued)

Figure 1:
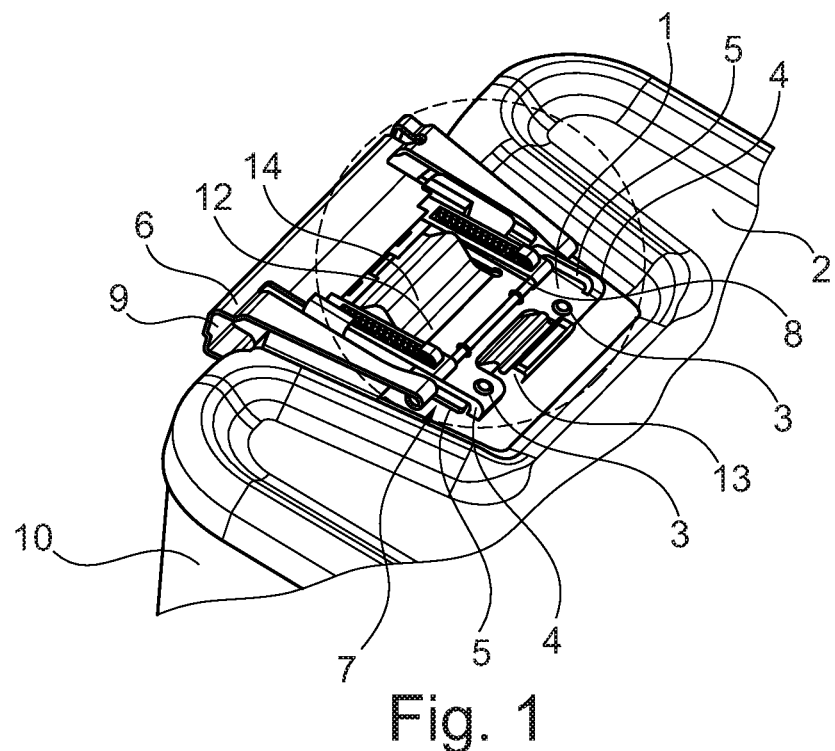

connectable to the bar element and which is integrated into the closure mechanism in such a way that the locking element blocks the closure mechanism when the closed position is reached.

12 Claims, 6 Drawing Sheets

(51) Int. Cl.
  *A61B 50/30*        (2016.01)
  *E05B 65/52*        (2006.01)

(58) Field of Classification Search
  CPC ............. E05B 65/5246; E05B 65/5269; E05B 65/5276; E05B 17/2034; E05B 17/2038; B65D 45/00; B65D 45/02; B65D 45/025; B65D 45/04; B65D 45/08; B65D 45/12; B65D 45/16; B65D 45/18; B65D 45/20; B65D 45/22; B65D 45/24; B65D 43/22; B65D 43/164; B65D 43/16; A61B 2050/007; A61B 2050/0074; A61B 50/00; A61B 50/30; E05C 1/00; E05C 1/004; E05C 1/06; E05C 1/065; E05C 1/02; E05C 1/08; E05C 1/12; E05C 1/14; E05C 1/145; E05C 1/166; E05C 1/04; Y10T 292/0913; Y10T 292/0914; Y10T 292/0917; Y10T 292/0886; Y10T 292/0887; Y10T 292/089; Y10T 292/0949; Y10T 292/20; Y10T 292/202
  USPC .................................. 220/326, 324, 830, 827
  See application file for complete search history.

(56) References Cited

U.S. PATENT DOCUMENTS

| | | | | |
|---|---|---|---|---|
| 5,706,968 A * | 1/1998 | Riley | ..................... | B65D 45/24 |
| | | | | 292/145 |
| 6,508,495 B1 | 1/2003 | Riley | | |
| 6,554,327 B1 * | 4/2003 | Riley | ........................ | E05C 1/04 |
| | | | | 24/642 |
| 6,592,000 B1 | 7/2003 | Owens et al. | | |
| 2008/0000899 A1 | 1/2008 | Baker et al. | | |
| 2021/0282879 A1 | 9/2021 | Thomas et al. | | |

FOREIGN PATENT DOCUMENTS

| | | | | | |
|---|---|---|---|---|---|
| DE | 102012101833 A1 * | 9/2013 | ............. | A61B 50/30 |
| DE | 102018117046 A1 | 1/2020 | | |
| JP | 2016155557 A | 9/2016 | | |
| JP | 2016169021 A * | 9/2016 | | |
| WO | WO-2008078169 A2 * | 7/2008 | ............. | A61B 50/30 |
| WO | 2020001932 A1 | 1/2020 | | |

OTHER PUBLICATIONS

Search Report received in International Application No. PCT/EP2021/059018 dated Jun. 29, 2021, with translation, 6 pages.
Written Opinion received in International Application No. PCT/EP2021/059018 dated Jun. 29, 2021, with translation, 16 pages.
Examination Report received in European Application No. 21 717 824.3 dated Mar. 20, 2024, with translation, 12 pages.

* cited by examiner

CLOSURE MECHANISM WITH LOCKING DEVICE FOR STERILE CONTAINERS, AND STERILE CONTAINER COMPRISING SAME

CROSS-REFERENCE TO RELATED APPLICATIONS

This application is the United States national stage entry of International Application No. PCT/EP2021/059018, filed Apr. 7, 2021, and claims priority to German Application No. 10 2020 109 765.4, filed Apr. 8, 2020. The contents of International Application No. PCT/EP2021/059018 and German Application No. 10 2020 109 765.4 are incorporated by reference herein in their entireties.

FIELD

The present invention relates to a closing mechanism for a sterile container having a container pan and a container lid lockable to the container pan via the closing mechanism, wherein the closing mechanism comprises a bar element for undercutting engagement with an engagement element forming an undercut on the container pan or on the container lid, respectively, wherein the bar element is positionable into a closed position, in which it is in undercutting operative connection with the engagement element, and into a release position, in which the bar element and the engagement element are disengaged.

BACKGROUND

Sterile containers described at the beginning are known from the prior art, which have a container pan that is hermetically sealable via a container lid as well as a closing mechanism, via which the lid is lockable to the pan in a fluid-tight manner. The so-called swing stopper is known for this purpose. It has an actuating lever which is pivotably mounted, for example on the lid, and to which a bracket or claw fastener/clamping jaw is hinged, which engages in an undercutting manner with a rail projecting laterally, for example on the container pan, and thus pulls the container lid against the container pan when the actuating lever is turned over. A sealing ring is arranged between the lid and the pan, which is pressed against the pan and the lid when the lid is tightened, thus sealing the contact area between the pan and the lid. Even small tolerances can be compensated for in the process.

For sterile containers, it is important that their internal pressure is at a predetermined ratio to the ambient pressure. In order to achieve this, sterile containers with a pressure equalization valve are known. In order to allow fluid (air, gas) to flow into the container interior from the environment (via a sterilizing filter device) and/or to allow fluid (air, gas) to flow out of the container interior into the environment (bypassing the filter device), it is known, for example, to arrange a valve device in the container lid. Decisive for a correct function of such a valve device is safe and fluid-tight locking of the lid on/at the container pan, in order to avoid unintentional leakages into/from the container at the contact point between pan and lid.

Another way of achieving pressure compensation in such sterile containers is to configure a closure mechanism in such a way that the lid can lift slightly from the container pan, even in the locked state, to compensate for excessive internal pressure in the container, so that fluid can flow out of the interior space. For this purpose, a sterile container is known having a closing/locking mechanism (hereinafter referred to as closing mechanism), a container pan and a container lid which is lockable to the container pan via the closing mechanism. The closing mechanism has an actuating lever, which is preferably pivotably mounted on the container lid or on the container pan, a pulling bracket/claw fastener/clamping jaw (hereinafter referred to as pulling bracket), which is coupled directly or indirectly to the actuating lever, and an engagement element on the container pan or on the container lid, which forms an undercut and with which the pulling bracket can be brought into undercutting operative connection in order to exert a tensile force on the engagement element in the direction in which the lid is placed on the container when the actuating lever is actuated. The pulling bracket is mounted so as to be displaceable transversely, preferably at a right angle to the tensile force to be exerted. A pre-tensioning element is also provided, for example in the form of a spring, which is arranged in an operative position relative to the pulling bracket in such a way that it only applies a compressive force to the pulling bracket in the direction of the tensile force to be exerted, i.e. in the direction in which the lid is placed on the container, when the actuating lever is in a predetermined actuating position and consequently in a predetermined/pre-determinable displacement position of the pulling bracket, in which the pulling bracket already engages behind the engagement element.

It is important for closing mechanisms and sterile containers that:

the container pan/the lower container part and/or the container lid/the upper container part and/or the closing mechanism is protected from damage as a result of unintended/incorrect actuation of the closing mechanism, in particular if the closing mechanism is provided with a lever function, wherein very large forces can arise, the largest possible area for marking the container/sterile container remains free on the front side of the lower container part despite the closing mechanism, accidental opening of the closure unit is prevented as far as possible, larger manufacturing tolerances can also be compensated for, and a minimum tightening force between the lid and the tray is ensured.

Furthermore, it would be desirable if:

the tensile force does not increase suddenly but continuously as the actuating lever is moved, in particular in order to prevent damage to the closing mechanism and/or to the seal, the closing mechanism can also assume a pressure relief valve function at the same time, the actuating lever is located in an easily accessible position, preferably on the upper side of the container lid, in order to avoid lateral protrusion also during the opening/closing process and not to cover the front side of the container pan, the closing mechanism is fixed in its closed/locked end position as stably as possible and is secured against unintentional/accidental opening, and the closing mechanism is particularly easy and quick to open from the closed/locked end position when it is deliberately actuated.

The disadvantage of known closing mechanisms or of sterile containers, respectively, is that they cannot achieve all of the above-mentioned properties.

SUMMARY

Against this background, the object of the present invention is to reduce the above-mentioned disadvantages of the prior art, in particular to provide a closing mechanism which is fixed as stably as possible in its closed end position (closed position) and is secured against unintentional/accidental opening, which can be opened particularly easily and quickly from the closed end position/closed position in the event of intentional actuation, and in which all, if possible, of the above-mentioned properties can be achieved.

The core idea of the present invention essentially consists in equipping the container closing mechanism according to the invention with a clamping jaw-like or claw fastener-like slider/bar element which is displaceably mounted, for example, on a container lid, wherein its claw fastener portion projects (preferably in principle, i.e. in each sliding position) over the container lid edge. At least one compression spring element is arranged between the slider/bar element and the container lid, which presses the slider/bar element increasingly away (upwards) from the container lid with increasing translational movement from its release position (far outside the container lid edge) into its closed position (near the container lid edge), i.e. lifts it upwards.

Furthermore, at least one return spring is arranged which pre-tensions the slider/bar element in the direction of its release position.

Finally, the slider/bar element or the compression spring element (connected to the slider for a joint sliding movement) is provided/configured with a (preferably manually operable or releasable) retaining element/retaining portion, which can be brought into retaining engagement (directly and in a latching manner) with a (preferably manually operable or releasable) locking/engagement element at or on the side of the container lid upon/with reaching the closed position, in order to hold the slider in the closed position against the pre-tensioning force of the return spring, in which the claw fastener portion engages under a container pan edge and pulls the container lid against the container pan edge as a result of the spring force of the at least one compression spring element, until the locking/engagement element on the side of the container lid or the retaining element/retaining portion on the side of the compression spring element is manually actuated for releasing the slider/bar element, and the slider/bar element springs back into its release position due to the return spring.

In other words, the aforementioned object according to the present invention is solved by a closing mechanism for/of a sterile container having a container pan and a container lid lockable to the container pan via the closing mechanism, wherein the closing mechanism comprises a claw-like bar element/slider for undercutting engagement with an engagement element (container pan edge/edge collar) forming an undercut configured on the container pan or on the container lid, wherein the bar element/slider is positionable in a closed position, in which it is in undercutting operative connection with the engagement element, and in a release position, in which the bar element and the engagement element are disengaged, wherein the closing mechanism has a locking element which is operatively connected or operatively connectable to the bar element/slider and which is integrated into the closing mechanism in such a way that it locks the closing mechanism in this closed position when the closed position is reached, in particular automatically/without separate user action.

The object is furthermore solved by a sterile container having a container lid and a container pan and a closing mechanism according to the invention, in particular with a closing mechanism according to the present description.

It is a particular advantage of the invention that the closing mechanism can be or is automatically secured in the closed position as a result of the built-in locking element. In particular, the closing mechanism may be configured in such a way that the locking element inevitably performs its locking function when the bar element is moved from the release position to the closed position, for example by being arranged in a fixed position relative to the container lid and coming into direct or indirect operative connection with the bar element, or by being arranged in a fixed position relative to the bar element and coming into operative connection with a counter latching structure arranged in a fixed position indirectly or directly on the container lid. In this way, accidental or unintentional opening of the closing mechanism can be prevented in a simple and safe manner.

The bar element is preferably a molded part/die-cut part made of metal or a plastic part. In particular, it may be configured in the shape of a hook, with a hook portion projecting at the edge over a side edge of the container lid for engaging behind the engagement element and a portion/slider portion adjoining the hook portion and projecting into the lid plane, which is guided/mounted on the container lid so that is positionable parallel to the lid plane. The bar element is preferably slidable parallel to the lid plane, that is between the release position, in which the hook portion and the engagement element are not engaged with each other, and the closed position, in which the hook portion and the engagement element are engaged with each other, the closing mechanism is locked, and the container lid is secured to the container pan. Therefore, it can also be said that the bar element is secured and locked in the closed position by the locking element.

Advantageous embodiments of the invention are explained in more detail below.

According to one embodiment, the closing mechanism may have a base plate which is configured and intended for arranging/fastening the closing mechanism to the container lid. The base plate, which is configured in particular as a metal-punched part/metal-formed part, may have a bearing structure for the bar element, preferably in the form of bent edge portions or collar portions. In these, elongated holes or grooves are preferably configured in which the bar element or a bearing structure connected to it is received and guided/mounted. The bar element is mounted so that it can be positioned linearly parallel to the lid plane. In addition, it may be pivotable transversely to the lid plane so that arranging/engaging the bar element with the engagement element of the container pan is being/is facilitated.

According to a particularly advantageous embodiment, the closing mechanism has a spring element that pre-tensions it into the release position. This spring element ensures that, if it was not secured by the locking element, the closing mechanism or the bar element would automatically assume the release position through pre-tension. According to the invention, however, the locking element also prevents unintentional/accidental transition of the closing mechanism from the closed position to the release position in this embodiment. Such a transition/movement is only possible as a result of the invention if the locking element is unlocked, for example, as a result of an actuation by the user. It is particularly advantageous and user-friendly that the closing mechanism automatically moves from the closed position to the release position after the locking element has been unlocked as a result of pre-tension by the spring element, without any further action by the user. In particular, the spring element may act directly on the bar element, for example by being arranged/supported on the bar element on the one hand and by being arranged/held in a positionally defined/stationary manner relative to the container lid on the other hand.

According to a further embodiment of the invention, the locking element may be configured and/or arranged to be elastic at least in sections. Alternatively, it may be configured to be completely elastic. For example, it may be configured as a locking-spring element or a locking-spring-damper element, in particular by a leaf spring element. It is of particular advantage if the locking element is configured to be elastically pre-tensioned. In particular, it may be configured as an elastically pre-tensioned rocker lever element (rocker lever) or an elastically pre-tensioned locking press button. Preferably, the locking element is configured and arranged in such a way that, when the closing mechanism/bar element reaches the closed position, it assumes the locking state locking the closing mechanism/bar element in the closed position due to its pre-tension. It is also advantageous if the locking element is configured and arranged in such a way that it can be transferred from the locking state to a release position releasing the closing mechanism/bar element by actuation by the user against its pre-tension.

The closing mechanism according to a further embodiment of the invention may have an actuating lever pivotably mounted on the container lid or on the container pan, respectively. This actuating lever may be coupled directly or indirectly to the bar element in such a way that the bar element can be positioned at least into the closed position via the actuating lever and, according to a further embodiment, can be positioned between the closed position and the locking state.

A further embodiment is characterized in that the bar element is configured and arranged in such a way that, in operative connection with the engagement element, it exerts a force (tensile force or compressive force) on the engagement element that causes the container lid to be pressed against the container pan. It is preferably configured and arranged to exert such a force when the closing mechanism is in the closed position. In this way, a particularly secure and tight fit of the lid on the container pan can be achieved, for example, by arranging/configuring an in particular elastic seal between them, which provides an additional sealing effect as a result of the contact force caused by the closing mechanism according to the invention.

Another embodiment of the invention is characterized in that the locking element has a spring portion. This may be arranged in the force flow between the container lid and the bar element. It can then advantageously exert a force on the bar element when the closing mechanism is in the closed position, which causes the bar element to be pressed against the engagement element. This force then opposes the contact force exerted by the closing mechanism between the container lid and the container pan. A particularly tight and secure fit both between lid and container as well as between bar element and engagement element is a particular advantage of this embodiment. In addition, in this embodiment, the spring portion or the locking element may provide a type of compensating element that ensures that a force exerted between the bar element and the engagement element in the closed position does not exceed an intended maximum value. This maximum value is determined by the spring characteristic and/or damper characteristic of the spring portion or of the locking element, respectively, and can be/is individually selected in such a way that a critical load on container pan and/or container lid and/or closing mechanism is not reached. In this embodiment, it is advantageous if the bar element can be pivoted transversely to the plane of the lid.

The locking element may have a latching structure, in particular in the form of a shoulder or a hook. When the closing mechanism reaches the closed position or is in the closed position, this latching structure engages with a counter latching structure preferably arranged or formed on the container lid and thus locks the closing mechanism in the closed position in a simple and reliable manner. Alternatively, the latching structure may engage with a counter latching structure arranged or formed on the bar element and thus lock the closing mechanism in the closed position in a simple and reliable manner. The locking or unlocking preferably takes place in a direction transverse to the direction of movement of the bar element, i.e. in particular transverse to the container lid plane or parallel thereto.

According to a further embodiment, the locking element is formed by a leaf spring. At least the spring portion of the locking element may be configured as a leaf spring. In such a leaf-spring-like locking element, the latching structure and the spring portion may be configured particularly efficiently and compactly in the form of a one-piece component, in particular may be shaped sheet metal parts made of a spring material, such as a spring steel.

In a further embodiment, the locking element may be a rocker lever arranged in a defined position on the container lid. In particular, this rocker lever may be pivotable relative to the bar element between a locking state that locks it in the closed position and a release position. The rocker lever is preferably pre-tensioned in the locking state, for example via a separate pre-tensioning element in the form of a spring/coil spring/leaf spring. It is of particular advantage if the rocker lever can be transferred from the locking state to its release position by an actuation pointing away from the container lid and the container pan, as in this way accidental unlocking of the closing mechanism by stacking several sterile containers on top of each other can be prevented in a simple and safe manner.

In summary, the invention can in particular bring about the following advantages:

It provides a closure unit for closing an upper container part/container lid with a lower container part/container pan, wherein preferably on a front side of the lower container part/container lid, despite the closure unit, the largest possible area, for example for marking the container, is free and available.

In particular, there is not necessarily any risk of the closure unit opening accidentally or of accidental actuation on the front side as a result of gripping/gripping around or pulling on the front face of the container.

The effect of the locking element/compensating element/spring portion also enables the closure unit to advantageously compensate for tolerances between the upper container part/container lid and the lower container part/container pan. In particular, the upper container part/container lid can be pressed onto the lower container part/container pan with a defined minimum force.

In the scope of one embodiment of the invention, a rotary movement of a folding handle/actuation element of the closure unit can be transformed into a trajectory of the bar element/slider, in which the force exerted by the closure on the container seal can increasingly increase.

In one embodiment, if there is an excess pressure in the container interior relative to the container exterior (or, in other words, if the container exterior exhibits a negative pressure relative to the container interior), a relative movement of the upper container part/container lid relative to the lower container part/container pan can take place. In this way, a bypass can be advantageously released between the upper container part/container lid and the lower container part/container pan.

An actuation element/folding handle for opening can be located in particular on the upper side of the upper container part/container lid. This results in optimized space conditions at the front and corresponding options for marking the containers at the front.

The distance from the folding handle/actuation element to the container opening is dimensioned in such a way that sufficient distance to the container interior is ensured, which is important, for example, for so-called aseptic provision in the operating room. It thus improves aseptic provision of the contents of the container.

When the closure is closed, it is stabilized/fixed/secured/ locked in the end position/closed position.

Accidental/unintentional opening of the closure can be easily and safely avoided/prevented.

Opening of the closure from the locking state is enabled particularly simply/user-friendly by actuating/unlocking the locking element.

BRIEF DESCRIPTION OF THE DRAWING FIGURES

Further features and advantages of the present invention will be apparent from the following exemplary and non-limiting description of the figures. These are merely schematic in nature and serve only to aid understanding of the invention.

Figure 2:
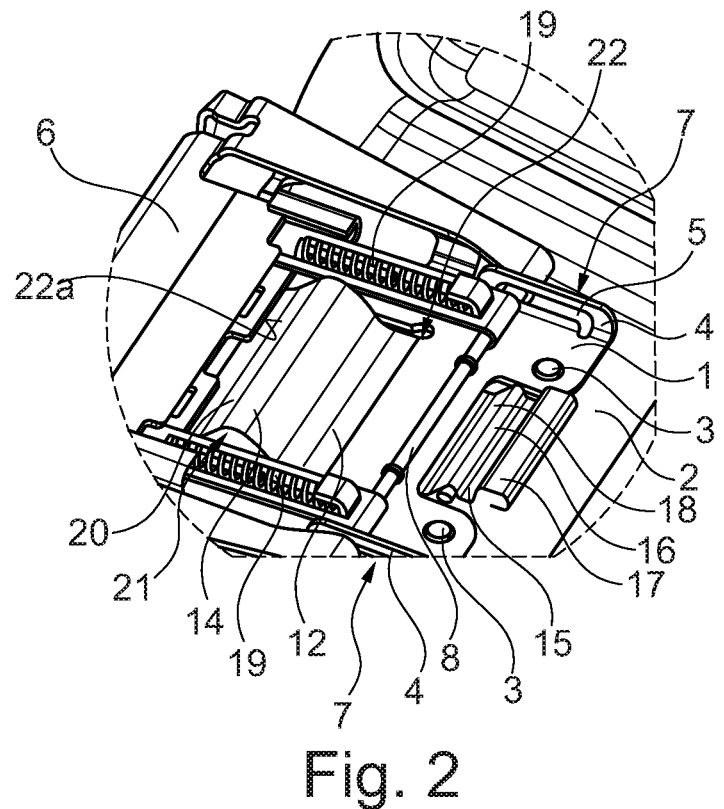
Figure 3:
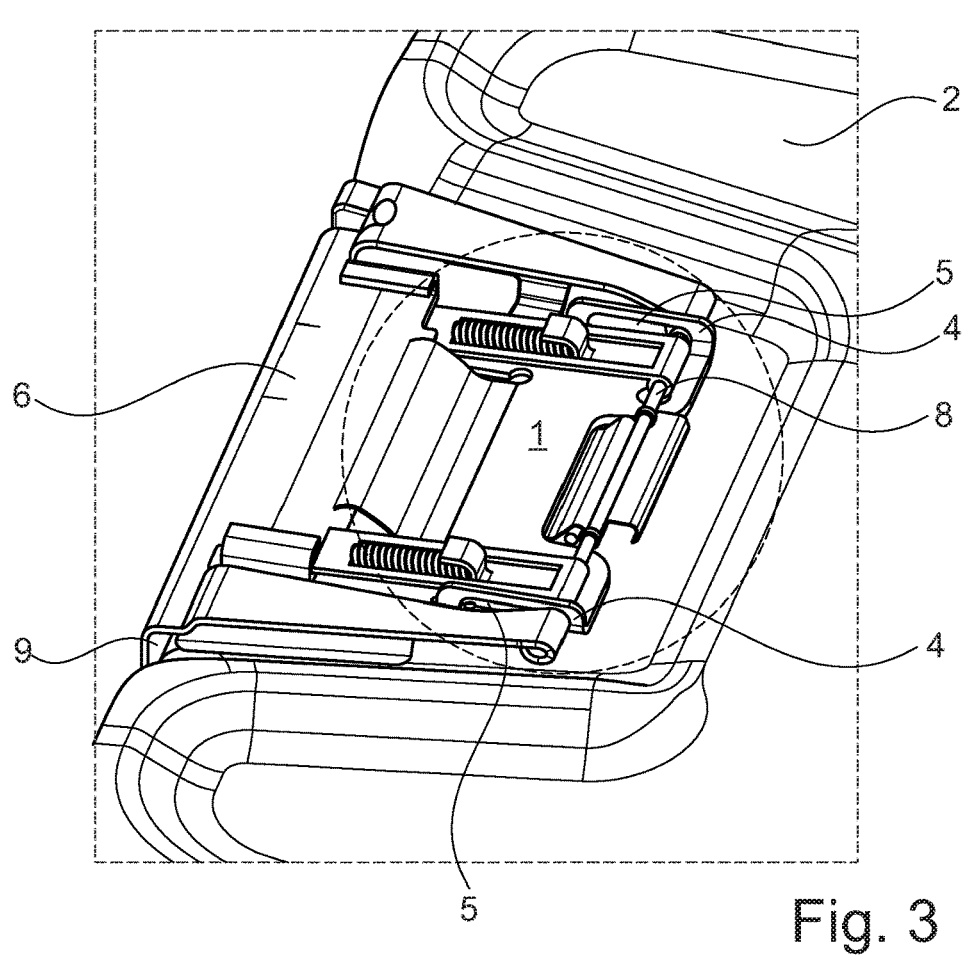
Figure 4:
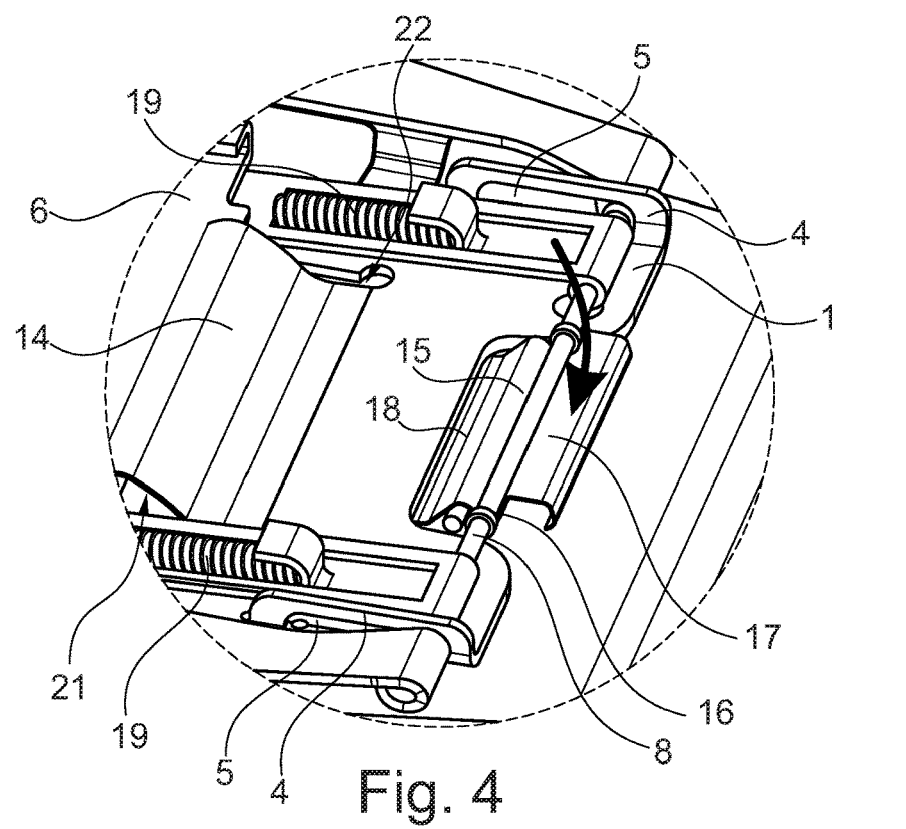
Figure 5:
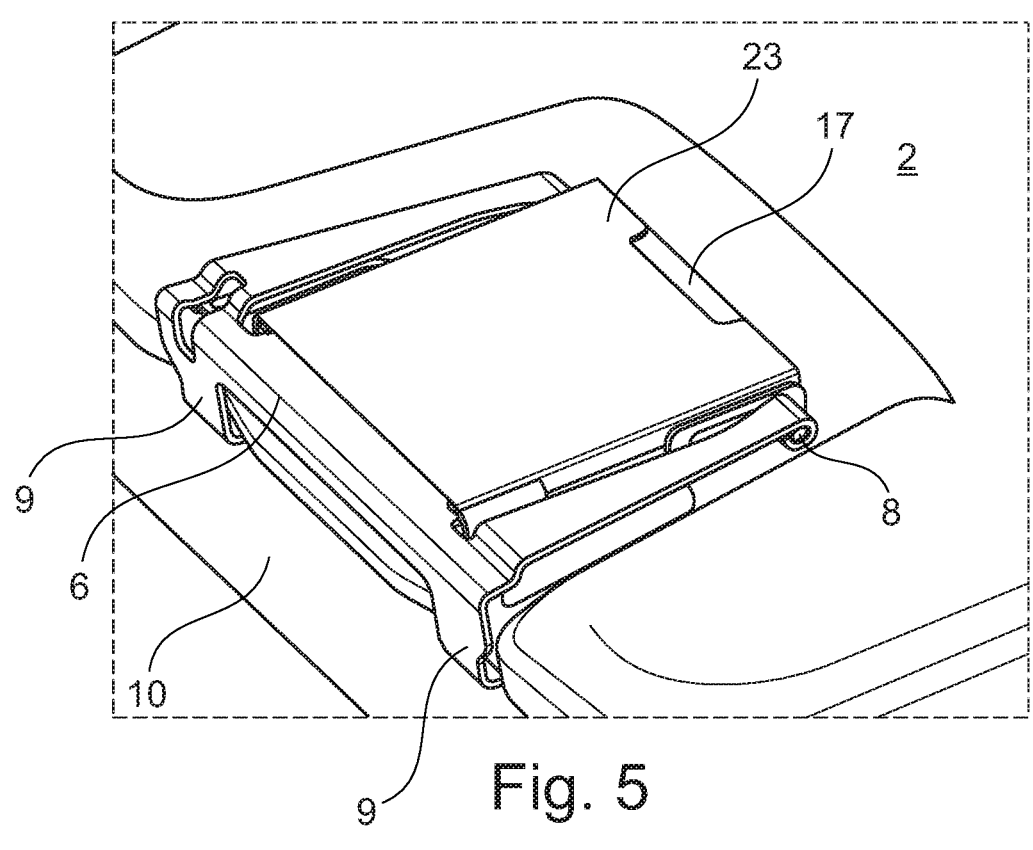
Figure 6:
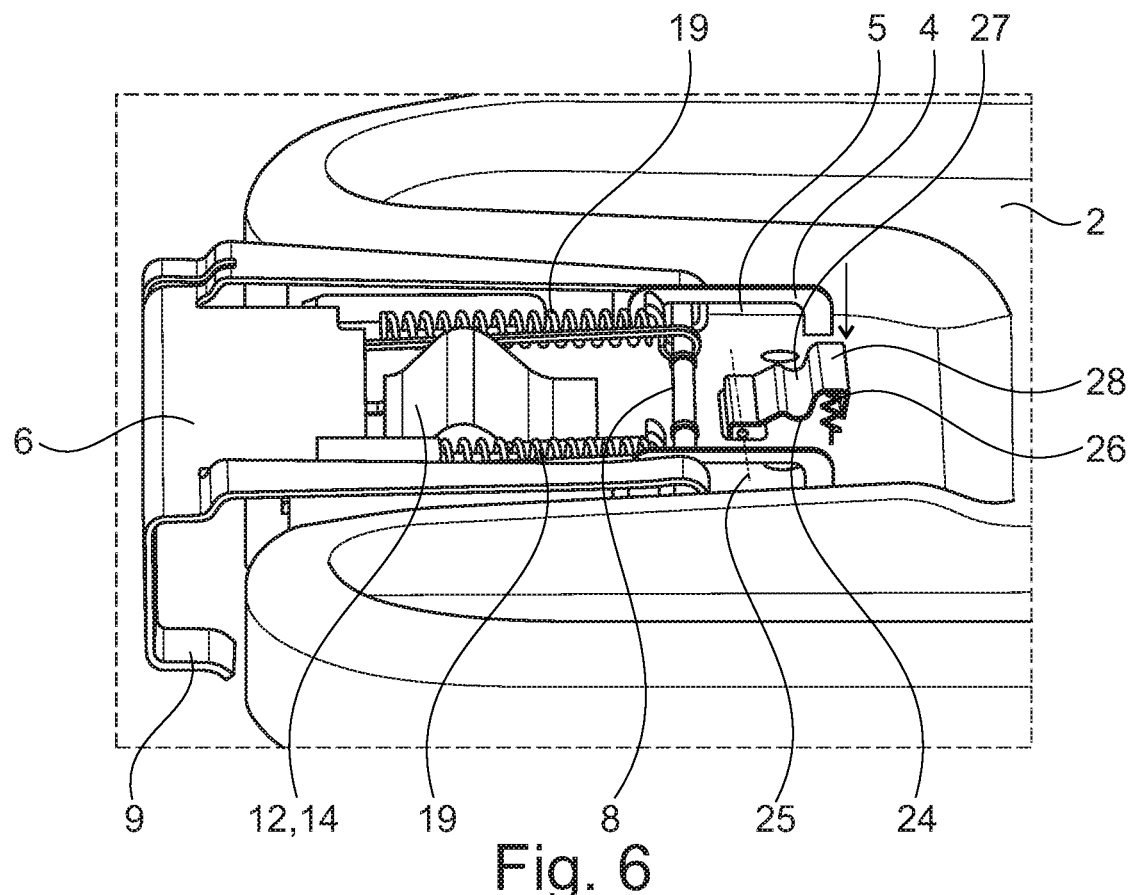
Figures 7, 8:
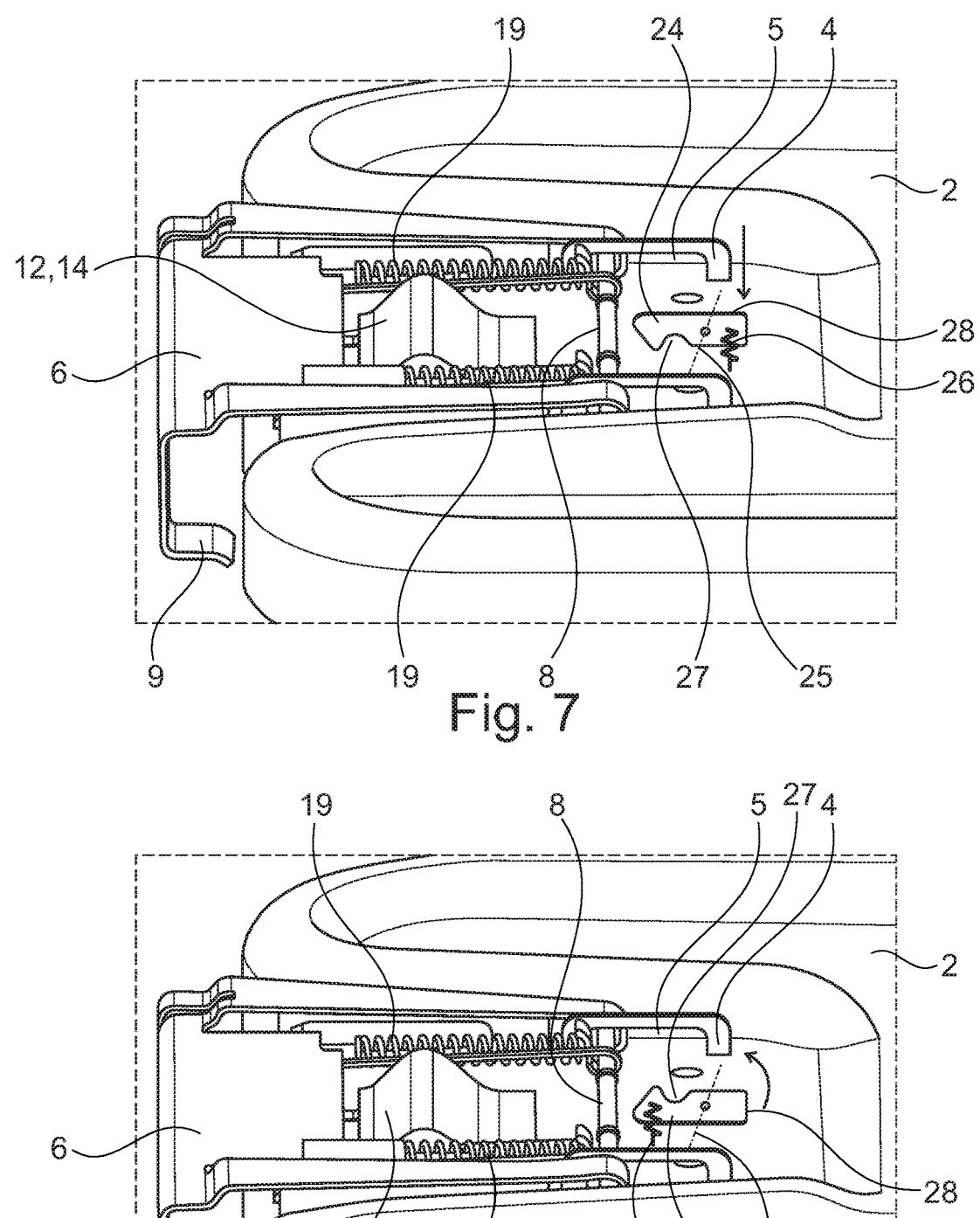
Figure 9:
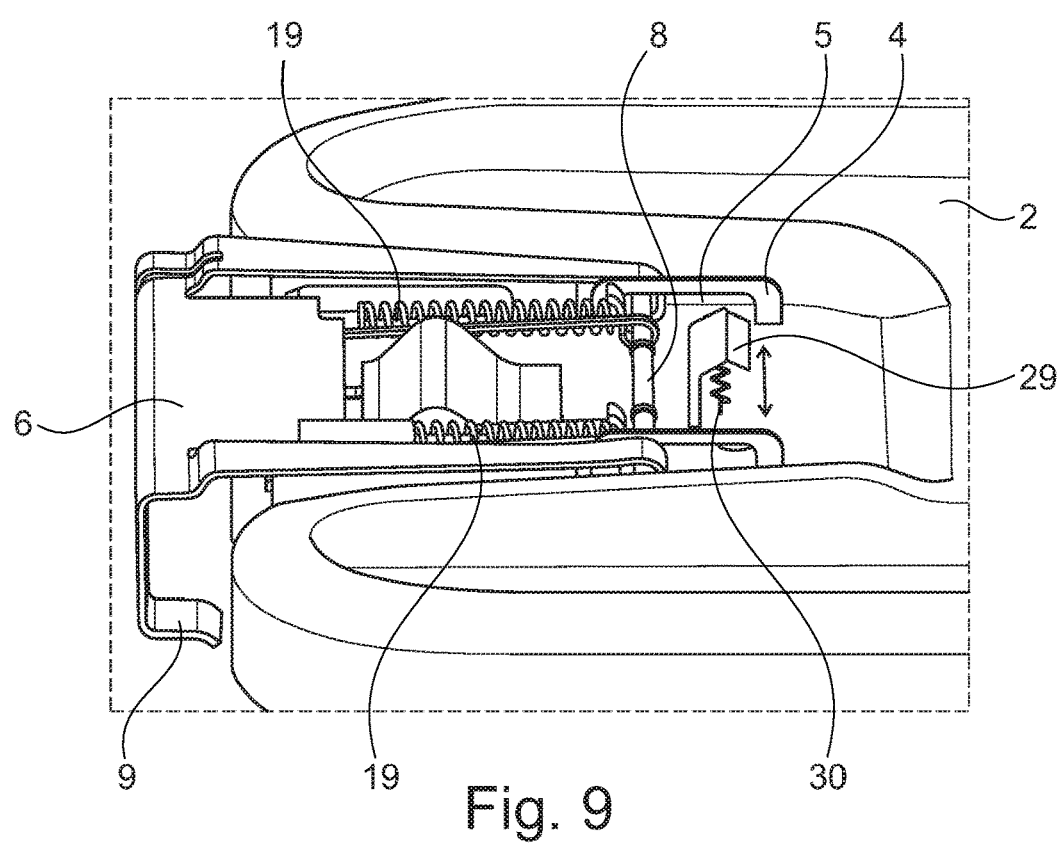
Figure 10:
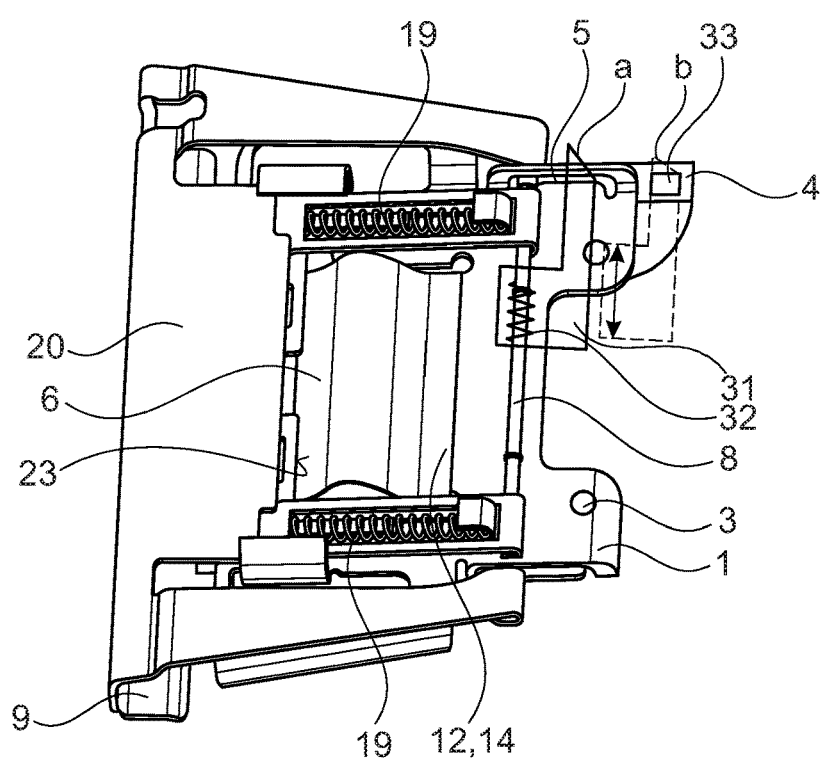
Figure 11:
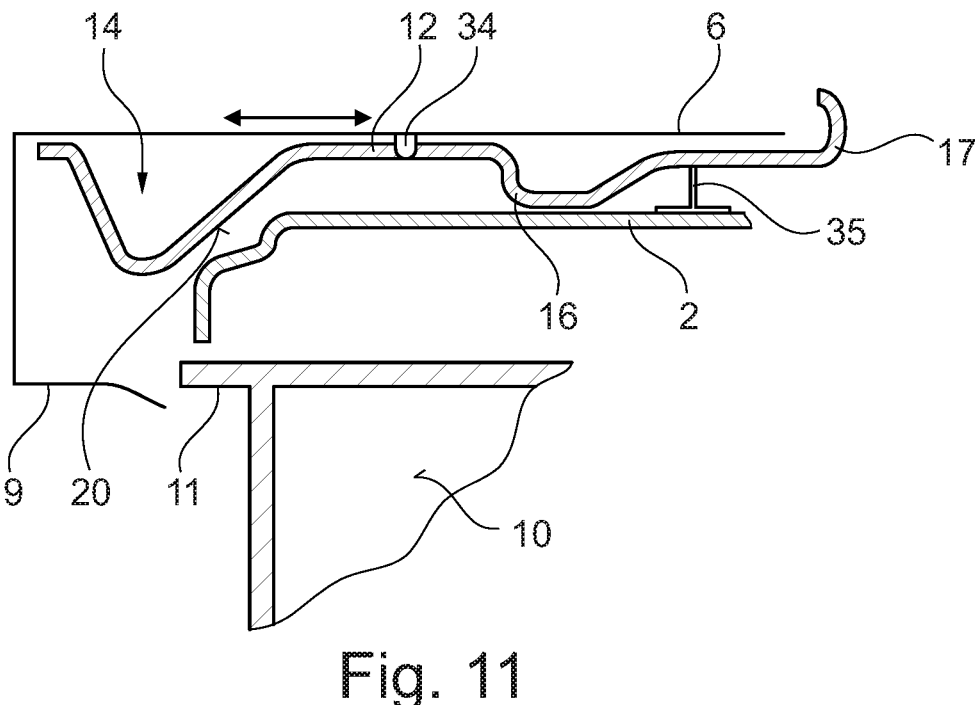
Figure 12:
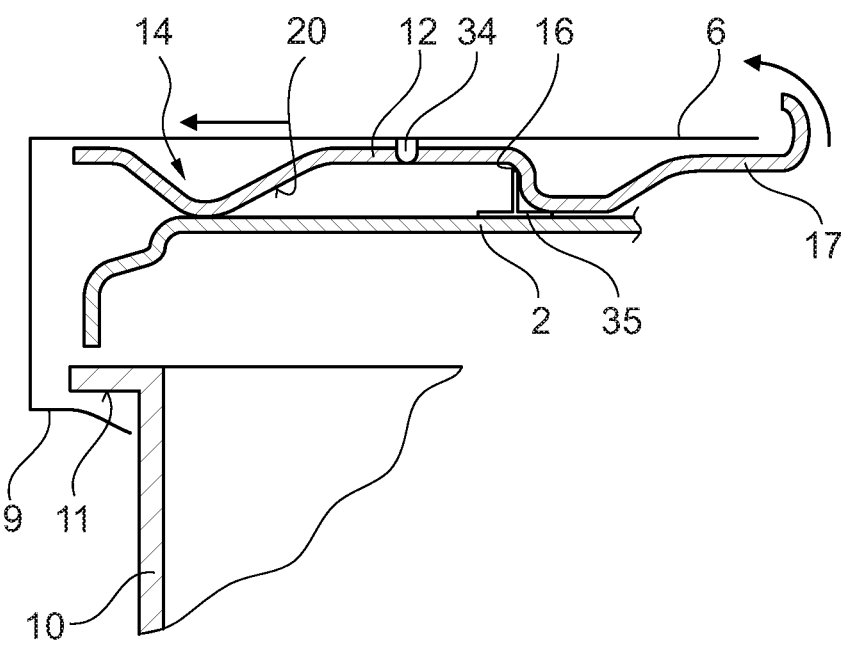

FIG. 1 is a perspective view of a closing mechanism according to a first configuration example of the invention in the open position, i.e. in the completely unlocked state, FIG. 2 is an enlarged detailed view of the closing mechanism of FIG. 1, FIG. 3 is a perspective view of the closing mechanism of FIGS. 1 and 2 in the closed position, i.e., in the fully closed state, FIG. 4 is an enlarged detailed view of the closing mechanism of FIG. 3, FIG. 5 is a perspective view of the closing mechanism of FIGS. 1 to 4 with a cover cap, FIG. 6 is a perspective view of a second configuration example in the open position, i.e. in the completely unlocked state, FIG. 7 is a perspective view of a third configuration example in the open position, i.e., in the completely unlocked state, FIG. 8 is a perspective view of a fourth configuration example in the open position, i.e. in the completely unlocked state, FIG. 9 is a perspective view of a fifth configuration example in the open position, i.e. in the completely unlocked state, FIG. 10 is a perspective view of a sixth configuration example in the open position, i.e. in the completely unlocked state, FIG. 11 is a sectional view of a closing mechanism according to a further configuration example in the open position, and FIG. 12 is a sectional view of the closing mechanism of FIG. 11 in the closed position.

DETAILED DESCRIPTION

A closing mechanism according to FIGS. 1 to 5 has a base plate 1 which is arranged on the upper side of a container lid 2 and is fastened, for example, via rivets 3. The base plate 1 is a punched, shaped sheet metal part and has collar portions 4 bent upwards on both sides by about 90° to the plane of the container lid 2. Each of these collar portions has a respective elongated guide hole 5 or a guide groove 5, the longitudinal direction of which extends essentially parallel to the plane of the container lid 2.

The closing mechanism also comprises a hook-shaped bar element 6, for example in the form of a pulling bracket/claw fastener/clamping jaw/locking slider 6. The bar element 6 is mounted on the upper side of a container lid 2 via a rod 8/axis 8/shaft 8 passing through the elongated guide holes 5 of the base plate 1 so as to be displaceable parallel to the latter. It is also pivotable in a certain region about the longitudinal axis of the rod 8 transverse to the plane of the container lid 2. Thus, it can be said that the collar portions 4 with the elongated guide holes 5 form guide motion links 7 or a support 7 for the bar element 6. Through this support 7, the bar element 6 can be positioned between an open position shown in FIGS. 1 and 2 and a closed position shown in FIGS. 3, 4 and 5, wherein the rod 8 slides in the elongated guide holes 7.

The bar element 6 has/forms a hook portion or claw portion 9 at its end projecting freely over the circumferential edge of the container lid 2, said hook portion or claw portion 9 being bent in the direction of the lower lid side or of a container pan 10, respectively. The hook portion or claw portion 9 is configured and provided to come into operative connection with a rail 11 formed on the circumferential side of the container pan 10 as an engagement element 11 undercutting the latter when the closing mechanism is in the closed position. When the closing mechanism is in the release position or open position, the hook portion or claw portion 9 and the engagement element 11 are not engaged with each other and the container lid 2 can be removed from the container pan 10. In the closed position, the container lid 2 is secured/fastened to the container pan 10.

The closing mechanism of the first embodiment of FIGS. 1 to 5 furthermore has a shaped sheet metal part 12. It contains several functions. On the one hand, it forms a locking element/locking portion 13 in the sense of the invention. On the other hand, it forms a leaf spring element/ leaf spring portion 14 for pre-tensioning/tensioning the bar element 6 with respect to the engagement element 11/the rail 11 of the container pan 10. While the locking element 13 and the leaf spring element 14 are configured in one piece by the shaped sheet metal part in the present configuration example, they may also be configured in multiple parts, in particular in two parts, by a plurality of shaped sheet metal parts in the scope of the invention.

In the embodiment of FIGS. 1 to 5, the locking element 13 is formed by a freely projecting arm of the shaped sheet metal part 12, which has spring properties. It has a latching structure 15, here in the form of an indentation 15, which forms an abutment shoulder 16. The width of the indentation 15 is slightly greater than the thickness of the rod 8. The distal free end of the locking element 13 is formed as an actuation element 17. On the side of the indentation 15 opposite the distal free end, the locking element 13 is provided with a guiding ramp 18 for the rod 8. Due to the spring properties of the locking element 13, it is pre-tensioned in a resting position protruding from the base plate 1. From this position, it can be resiliently displaced against its spring pre-tension in the direction of the base plate 1.

When the closing mechanism and thus the bar element 6 are in the release position/open position, the rod 8 and the locking element 13 are disengaged. This situation is shown in FIGS. 1 and 2. The rod 8 is positioned on the side of the indentation 15 and the guiding ramp 18 opposite from the actuation element 17. As shown in particular in FIGS. 3 and 4, the rod 8 comes to rest in the indentation 15 when the bar element 6 is in the closed position. When the bar element 6 is moved from the release position to the closed position, the rod 8 is displaced together with the bar element 6 in the direction towards the locking element 13. The rod 8 runs onto the guiding ramp 18 of the locking element 13. Since the bar element 6 and the rod 8 in the guide motion link 7 are preferably guided parallel to the plane of the container lid 2, the locking element 13 is displaced by the rod 8 against its pre-tension in the direction of the container lid 2 and the base plate 1 during continued movement into the closed position. It can also be said that the locking element 13 deflects in the direction towards the base plate 1 or towards the container lid 2, respectively. As soon as the rod 8 overlaps with the indentation 15, the locking element 13 springs back into its resting position at a distance from the base plate as a result of its spring properties. The rod 8 then comes to rest in the indentation 15 and in contact with the shoulder 16. The bar element 6 is thus secured in the closed position by the locking element 13. In this way, the indentation 15 forms a latching structure with the shoulder 16, and the rod 8 forms a counter latching structure in the sense of the invention that interacts with it.

The closing mechanism also has two coil springs 19 as spring elements 19, which pre-tension in the release position/open position. The coil springs 19 are each supported on the one hand on the bar element 6 and on the other hand on the base plate 1. When the bar element 6 is moved into the closed position, the coil springs 19 are compressed against their spring tension. In order to move the closing mechanism and the bar element 6 from the closed position to the release position, the user has to actuate the actuation element 17, which is pressed and displaced against the spring tension of the locking element 13 in the direction of the base plate 1 or of the container lid 2, respectively. As a result of this displacement, the shoulder 16 and the rod 8 are disengaged and, due to the tension of the coil springs 19, the bar element 6 is displaced from the closed position back into the release position.

The leaf spring element 14 formed by the shaped sheet metal part 12 has a ramp surface 20 projecting away from the plane of the container lid 2, which is formed by a wave-shaped or roof-shaped region 21. This roof-shaped region 21 also projects from the plane of the container lid 2 or of the base plate 1, respectively, and into a recess 22/window 22 formed in the bar element 6. When the bar element 6 is moved into the closed position, an edge 22a bounding the recess 22 interacts with the ramp surface 20 of the region 21 and runs onto it. On the one hand, this may result in elastic deformation of the roof-shaped region 21 or of the ramp surface 20 in the direction of the base plate and, on the other hand, in displacement of the hook portion or claw portion 9, since the bar element 6 is guided relative to the base plate 1 and the container lid 2 only on its distal free side via the rod 8 and the guide 7, but is otherwise rotatable about the rod 8. The kinematics are configured and adjusted in such a way that the hook portion or claw portion 9 does not result in or start pivoting away from the base plate 1 as a result of the interaction with the ramp surface 20 until the hook portion or claw portion 9 engages behind the rail 11 of the container pan 10. In this way, the closing mechanism on the one hand causes the hook portion or claw portion 9 to be tensioned with the rail 11 (and thus a tight fit) and on the other hand, due to the elasticity of the roof-shaped region 21, has a type of overload protection which defines pressing of the container lid 2 against the container pan 10 by the spring force acting in the process.

FIG. 5 shows that the closing mechanism shown in FIGS. 1 to 4 is largely covered via a cover 23, which leaves only the actuation element 17 free.

FIG. 6 shows a perspective view of a further configuration example of the closing mechanism in the open position, which differs from the embodiment of FIGS. 1 to 5 only in the configuration of the locking element. In this embodiment, a shaped sheet metal part 12 forms only the leaf spring element 14. A rocker lever 24 (i.e., actuating lever) is formed separately from the shaped sheet metal part 12 and constitutes a locking element in the sense of the invention. The rocker lever 24 is arranged on the base plate 1 (or on the container lid 2) so as to be fixed in position and pivotable about a pivot axis 25. It is positionable between a resting position/locking position, in which it is pre-tensioned via a compression spring 26, and a release position, into which it can be brought by user actuation against the force of the compression spring 26. The rocker lever 24 has an indentation 27 or a hook 27 open in the direction away from the base plate and configured and intended to receive/interact with the rod 8 when the bar element 6 is in the closed position. The end of the rocker lever 24 remote from the pivot axis 25 is configured as an actuation element 28 for pressure actuation by a user. Accordingly, the rocker lever 24 can lock the bar element 6 in the locking position and releases it for movement in the release position.

When the bar element 6 is brought into the closed position, the rod 8 runs onto the rocker lever 24. As a result, the rocker lever 24 pivots against the force of the compression spring 26 in the direction of the container lid 2/base plate 1 until the rod 8 overlaps with the indentation 27 and the rocker lever 24 pivots back into its resting position due to the action of the compression spring 26. In this position, the rod 8 lies in the indentation 27 so that the bar element 6 is locked in the closed position. When the actuation element 28 is pressed in the direction of the base plate 1, the indentation 27 releases the rod 8 and the bar element 6 automatically returns from the closed position to the release position due to the pre-tension of the coil springs 19.

FIG. 7 shows a perspective view of the closing mechanism according to a further configuration example in the open position. This is essentially similar to that of FIG. 6, but differs in the arrangement of the pivot axis 25 and the orientation of the indentation 27 of the rocker levers 24, which is open in the direction of the base plate.

FIG. 8 shows another configuration example in which the indentation 27 of the rocker lever 24 is still open at the top (i.e. open on the side facing away from the base plate 1), and the compression spring 26 and the indentation 27 are arranged on one side of the pivot axis 25, and the actuation element 28 is arranged on the side of the pivot axis 25. It is a particular advantage of this embodiment that the actuation element 28 is not pressure actuable in the direction of the base plate 1 and the container lid 2, but is actuable by a pull actuation in a direction away from the base plate 1 and the container lid 2. This prevents accidental actuation of the actuation element 28 and unlocking of the bar element 6 and the closing mechanism when several sterile containers 10 are stacked on top of each other.

FIG. 9 shows a perspective view of a further configuration example of the invention in the open position. Here, instead of a rocker lever 24, a press button 29 is provided as a locking element, which is configured and intended to interact with the rod in a manner already described with reference to the other configuration examples and is pre-tensioned with a compression spring 30 into a locking state that locks the rod 8.

FIG. 10 shows a configuration example of the invention in which the locking element is formed in the form of a locking element 31 that is positionable transversely to the plane of the container lid 2 and the base plate 1. The locking element 31 is mounted on the rod 8 in the longitudinal direction thereof so as to be relatively positionable between a locking state and a release position. It is also pre-tensioned into the locking state via the spring element 32. Compared to the other configuration examples, the collar section 4 of the base plate 1 is configured to be elongated and has a locking recess 33 into which the locking element 31 automatically engages/can engage when the closing mechanism/bar element 6 is in the closed position due to the pre-tensioning by the spring element 32. In order to move the closing mechanism from the closed position to the release position, the locking element 31 is actuated against the spring pre-tension by the user and the locking recess 33 is disengaged, so that the bar element 6 changes independently to the release position due to the tension of the coil springs 19. While FIG. 10 shows only one locking element 31 on one side of the closing mechanism, a variant of this configuration example may have two such locking elements 31 arranged on both sides of the closing mechanism.

FIG. 11 shows a sectional view of a further configuration example in the open position, which differs from the configuration example of FIGS. 1 to 5 in that the shaped sheet metal part 12 is not stationarily fixed to the container lid 2, but is fixed stationarily to the bar element 6. FIG. 12 shows a sectional view of the closing mechanism of FIG. 11 in the closed position. The shaped sheet metal part 12 can, for example, be connected to the bar element 6 by a rivet connection or screw connection 34 or a material connection 34 (spot welding, etc.). A latching element 35 may be arranged on the container lid 2 or on the base plate 1, which is configured to interact with the locking element 13 of the shaped sheet metal part 12. Moreover, the configuration example of FIGS. 11 and 12 corresponds to that of FIGS. 1 to 5, so that reference is made to the description of further details given there. A particular advantage of this configuration example is that the shaped sheet metal part 12 is almost completely covered and protected by the bar element 6, irrespective of its functional position, and that the locking element 13 is unlocked by a pull actuation of the actuation element 17 (unlike the configuration example of FIGS. 1 to 5, in which a push actuation takes place in the direction of the container lid), so that unintentional unlocking can be safely avoided when several sterile containers are stacked on top of each other.

The invention claimed is:

1. A closing mechanism for a sterile container, the sterile container having a container pan and a container lid, the container lid lockable to the container pan via the closing mechanism, the closing mechanism comprising a base plate with collar portions and a bar element configured for displaceable support on the container lid or on the container pan for undercutting engagement with an engagement element forming an undercut on the container pan or on the container lid, the bar element being positionable or displaceable into:

a closed position, in which the bar element is in undercutting operative connection with the engagement element; and a release position, in which the bar element and the engagement element are disengaged, the closing mechanism comprising a locking element operatively connectable to the bar element, the locking element being integrated into the closing mechanism or interacting with the closing mechanism in such a way that the bar element locks the closing mechanism in the closed position when the closed position is reached, and the locking element comprising a latching structure that engages with a counter latching structure, the counter latching structure being a shaft that is arranged or formed on the bar element when the closing mechanism is in the closed position, wherein the bar element comprises a slider portion, configured to extend along a container lid plane and to be slidable parallel to the container lid plane, and the shaft is configured to slide in elongated holes of the collar portions between the closed position and the release position of the bar element, wherein the bar element is fully out of engagement with the locking element in the release position.

2. The closing mechanism according to claim 1, further comprising a spring element or return spring that pre-tensions the closing mechanism into the release position.

3. The closing mechanism according to claim 1, wherein the locking element is elastic or is formed by a spring element, or the locking element is configured to be elastically pre-tensioned; and wherein, when the locking element has a pre-tension and the closing mechanism reaches the closed position, the locking element assumes a locking state locking the closing mechanism in the closed position due to the pre-tension, and locking element being transferrable from the locking state to a release position releasing the closing mechanism by user actuation against the pre-tension.

4. The closing mechanism according to claim 1, wherein the bar element is configured and arranged in such a way that, in operative connection with the engagement element, the bar element exerts a tensile force or a compressive force on the engagement element that causes the container lid to be pressed against the container pan.

5. The closing mechanism according to claim 1, further comprising an actuating lever that is pivotably mountable on the container lid or on the container pan, the actuating lever being coupled directly or indirectly to the bar element in such a way that the bar element is retained in the closed position via the actuating lever.

6. The closing mechanism according to claim 1, wherein the closing mechanism has a spring element configured to press the bar element against the engagement element, and the locking element comprises a freely projecting arm having spring properties that cause the locking element to exert a force on the bar element when the closing mechanism is in the closed position.

7. The closing mechanism according to claim 1, wherein the locking element comprises a leaf spring or is configured by a leaf spring.

8. The closing mechanism according to claim 1, wherein the locking element is a rocker lever arranged in a defined position on the container lid, the rocker lever being pivotable relative to the bar element between:

a locking state that locks the rocker lever in the closed position, and a rocker lever release position, wherein the rocker lever is pre-tensioned.

9. The closing mechanism according to claim 8, wherein the locking element is transferrable from the locking state to the rocker lever release position by an actuation pointing away from the container lid.

10. The closing mechanism according to claim 1, wherein the latching structure of the locking element is formed as an indentation that is configured to receive the shaft as the counter latching structure, and in which the shaft comes to rest when the closing mechanism is in the closed position.

11. A sterile container comprising a container lid, a container pan and a closing mechanism comprising a bar element configured for displaceable support on the container lid or on the container pan for undercutting engagement with an engagement element, the bar element being positionable or displaceable into:

a closed position, in which the bar element is in undercutting operative connection with the engagement element; and a release position, in which the bar element and the engagement element are disengaged, the closing mechanism comprising a locking element operatively connectable to the bar element, the locking element being integrated into the closing mechanism or interacting with the closing mechanism in such a way that the bar element locks the closing mechanism in the closed position when the closed position is reached, and the locking element comprising a latching structure that engages with a counter latching structure that is arranged or formed on either the container lid or on the bar element when the closing mechanism is in the closed position, wherein:

the engagement element forms an undercut on the container pan, and the bar element is displaceably mounted on the container lid, and the bar element comprises a claw fastener portion projecting laterally over an edge of the container lid for undercutting engagement with the engagement element, at least one compression spring element is arranged between the bar element and the container lid, the at least one compression spring element pressing the bar element increasingly away from the container lid with increasing translational movement from the release position into the closed position, at least one return spring comprising a pre-tension that pre-tensions the bar element toward the release position, wherein the at least one compression spring element is configured to bias the latching structure and the counter latching structure together when the closing mechanism is in the closed position in order to hold the bar element in the closed position against the pre-tension of the at least one return spring, and the at least one compression spring element is configured to bias the claw fastener portion against the engagement element to pull the container lid against a container pan edge, until the locking element or the engagement element on a side of the container lid or the at least one compression spring element is manually actuated for releasing the bar element, and the bar element springs back into the release position due to the at least one return spring.

12. A container lid comprising a closing mechanism, the container lid being lockable to a container pan via the closing mechanism, the closing mechanism comprising a base plate with collar portions and a bar element configured for displaceable support on the container lid for undercutting engagement with an engagement element forming an undercut on the container pan, the bar element being positionable or displaceable into:

a closed position, in which the bar element is in undercutting operative connection with the engagement element; and a release position, in which the bar element and the engagement element are disengaged, the closing mechanism comprising a locking element operatively connectable to the bar element, the locking element being integrated into the closing mechanism or interacting with the closing mechanism in such a way that the bar element locks the closing mechanism in the closed position when the closed position is reached, and the locking element comprising a latching structure that engages with a counter latching structure, the counter latching structure being a shaft that is arranged or formed on the bar element when the closing mechanism is in the closed position, wherein the bar element comprises a slider portion, configured to extend along a container lid plane and to be slidable parallel to the container lid plane, and the shaft is configured to slide in elongated holes of the collar portions between the closed position and the release position of the bar element, wherein the bar element is fully out of engagement with the locking element in the release position.

* * * * *